United States Patent [19]
McCurry, Jr. et al.

[11] Patent Number: 5,362,861
[45] Date of Patent: Nov. 8, 1994

[54] CONTINUOUS BLEACHING OF ALKYLPOLYGLYCOSIDES

[75] Inventors: Patrick M. McCurry, Jr., Lansdale, Pa.; Robert L. Klein, Jr., Libertyville, Ill.; Michael W. Gibson, Fairfield, Ohio; James D. Beaulieu, Humble, Tex.; Janet R. Varvil, Chalfont, Pa.

[73] Assignee: Henkel Corporation, Plymouth Meeting, Pa.

[21] Appl. No.: 914,363

[22] Filed: Jul. 15, 1992

[51] Int. Cl.$^5$ .................. C07H 15/04; C07H 1/06
[52] U.S. Cl. .................... 536/4.1; 536/120; 536/127
[58] Field of Search ............. 536/127, 124, 120, 18.6, 536/4.1

[56] References Cited

U.S. PATENT DOCUMENTS

| | | | |
|---|---|---|---|
| 2,235,783 | 9/1939 | White | 536/18.6 |
| 2,356,565 | 8/1944 | Chwala | 536/18.6 |
| 2,390,507 | 12/1945 | Cantor | 536/18.6 |
| 2,422,328 | 6/1947 | Young | 106/126 |
| 3,219,656 | 11/1965 | Boettner | 536/18.3 |
| 3,375,243 | 3/1968 | Nevin et al. | 536/18.6 |
| 3,450,690 | 6/1969 | Gibbons et al. | 536/18.5 |
| 3,547,828 | 12/1970 | Mansfield et al. | 252/351 |
| 3,598,865 | 8/1971 | Lew | 536/18.6 |
| 3,640,998 | 2/1972 | Mansfield et al. | 536/18.3 |
| 3,707,535 | 12/1972 | Lew | 536/18.6 |
| 3,721,633 | 3/1973 | Ranauto | 252/527 |
| 3,737,426 | 6/1973 | Throckmorton et al. | 536/18.6 |
| 3,772,269 | 11/1973 | Lew | 536/18.6 |
| 3,839,318 | 10/1974 | Mansfield | 536/18.6 |
| 3,974,138 | 8/1976 | Lew | 536/4.1 |
| 4,011,389 | 3/1977 | Langdon | 536/4.1 |
| 4,223,129 | 9/1980 | Roth et al. | 536/4.1 |
| 4,349,669 | 9/1982 | Klahr et al. | 536/127 |
| 4,393,203 | 7/1983 | Mao et al. | 536/124 |
| 4,472,170 | 9/1984 | Hellyer | 536/18.6 |
| 4,510,306 | 4/1985 | Langdon | 536/127 |
| 4,557,729 | 12/1985 | McDaniel et al. | 536/124 |
| 4,597,770 | 7/1986 | Forand et al. | 536/18.6 |
| 4,704,453 | 11/1987 | Lorenz et al. | 536/18.6 |
| 4,713,447 | 12/1987 | Letton | 536/18.6 |
| 4,904,774 | 2/1990 | McDaniel et al. | 536/127 |
| 4,950,743 | 8/1990 | McCurry et al. | 536/124 |
| 4,987,225 | 1/1991 | Pickens et al. | 536/124 |
| 4,990,605 | 2/1991 | Lueders | 536/18.5 |
| 5,003,057 | 3/1991 | McCurry et al. | 536/18.6 |

FOREIGN PATENT DOCUMENTS 0092355 10/1983 European Pat. Off. .
0096917 12/1983 European Pat. Off. .
0132043 12/1987 European Pat. Off. .

Primary Examiner—Johnnie R. Brown
Assistant Examiner—Everett White
Attorney, Agent, or Firm—Ernest G. Szoke; Wayne G. Jaeschke; Patrick J. Span

[57] ABSTRACT

A continuous method of bleaching an alkylpolyglycoside, substantially free of alcohol, with peroxy compounds, preferably hydrogen peroxide, which is highly efficient to provide an unexpected high degree of color reduction from a dark brown to a light, white product, from an extinction coefficient color respectively of about 10 to about 15 to about 0.025 to about 0.15. The bleaching is carried out at controlled pH and temperature, under pressure preferably in the presence of Mg or MgO.

22 Claims, 2 Drawing Sheets

CONTINUOUS BLEACHING OF ALKYLPOLYGLYCOSIDES

BACKGROUND OF THE INVENTION

1. Field of the Invention

This invention relates to an improved method for bleaching alkylpolyglycosides, and in particular to a continuous method of bleaching with a peroxide, such as hydrogen peroxide.

2. Description of Related Art

Alkyl glycosides are conveniently prepared by reacting an alcohol of the type and chain length which is desired to form the "alkyl" portion of the glycoside of interest with a saccharide reactant (e.g., a monosaccharide such as glucose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl glycoside product of interest. Typically, such reaction is conducted at an elevated temperature and in the presence of an acid catalyst. Various alkyl glycoside products and processes for making same are disclosed in a variety of representative patents. U.S. Pat. No. 4,987,225 contains an extensive listing of processes for preparing alkyl glycoside compositions. As disclosed therein, processes for preparing alkyl glycoside compositions are disclosed in U.S. Pat. No. 3,219,656 to Boettner (issued Nov. 23, 1965); U.S. Pat. No. 3,547,828 to Mansfield et al. (issued Dec. 15, 1970); U.S. Pat. No. 3,598,865 to Lew (issued Aug. 10, 1971); U.S. Pat. No. 3,707,535 to Lew (issued Dec. 26, 1972); U.S. Pat. No. 3,772,269 to Lew (issued Nov. 13, 1973); U.S. Pat. No. 3,839,318 to Mansfield (issued Oct. 1, 1974); U.S. Pat. No. 4,349,669 to Klahr (issued Sep. 14, 1982); U.S. Pat. No. 4,393,203 to Mao et al. (issued Jul. 12, 1983); U.S. Pat. No. 4,472,170 to Hellyer (issued Sep. 18, 1984); U.S. Pat. No. 4,510,306 to Langdon (issued Apr. 9, 1985); U.S. Pat. No. 4,597,770 to Forand et al. (issued Jul. 1, 1986); U.S. Pat. No. 4,704,453 to Lorenz et al. (issued Nov. 3, 1987); U.S. Pat. No. 4,713,447 to Letton (issued Dec. 15, 1987); published European Application No. 83302002.7 (EPO Publication No. 0092355; Vander Burgh et al; published Oct. 26, 1983); published European Application No. 83200771.0 (EPO Publication No. 0096917; Farris; published Dec. 28, 1983); and published European Application No. 84303874.6 (EPO Publication 0132043; published Jan. 23, 1985). Other representative patents are U.S. Pat. No. 2,235,783 (White, issued Mar. 18, 1941); U.S. Pat. No. 2,356,565 (Chwala, issued Aug. 22, 1944); U.S. Pat. No. 2,390,507 (Cantor, issued Dec. 11, 1945); U.S. Pat. No. 2,442,328 (Young, issued Jun. 17, 1947); U.S. Pat. No. 3,375,243 (Nevin et al., issued Mar. 26, 1968); U.S. Pat. No. 3,450,690 (Gibbons et al., issued Jun. 17, 1969); U.S. Pat. No. 3,640,998 (Mansfield et al., issued Feb. 8, 1972); U.S. Pat. No. 3,721,633 (Ranauto, issued Mar. 20, 1973); U.S. Pat. No. 3,737,426 (Throckmorton et al., issued Jun. 5, 1973); U.S. Pat. No. 3,974,138 (Lew, issued Aug. 10, 1976); U.S. Pat. No. 4,011,389 (Langdon, issued Mar. 8, 1977); and U.S. Pat. No. 4,223,129 (Roth et al., issued Sep. 16, 1980).

In the preparation of alkyl glycoside products, it is not uncommon for such products to develop an undesirably dark coloration during the course of the synthesis and isolation procedures employed. Various procedures have been suggested for improving the color of such dark colored glycoside products including, for example, treatment with bleaching reagents such as hydrogen peroxide; intentional color formation by heat treatment under alkaline conditions followed by removal (e.g., by precipitation, filtration, etc.) of dark colored impurities generated during said treatment procedure; treatment with decolorizing adsorbents such as particulate carbon materials, etc.; and the like. See in this regard, for example, Gibbons' U.S. Pat. No. 3,450,690 which discloses an alkaline heat treatment/separation procedure that can optionally be followed by treatment with bleaching agents such as hydrogen peroxide or by treatment with decolorizing carbons. See also Cantor's U.S. Pat. No. 2,390,507; White's U.S. Pat. No. 2,235,783; Example 1 of Throckmorton et al.'s U.S. Pat. No. 3,737,426; Examples 5 and 10 of Langdon's U.S. Pat. No. 4,011,389; and Example 1 of U.S. Pat. No. 4,472,170 to Hellyer (issued Sep. 18, 1984) for teachings related to the use of carbon adsorbents for the decolorization of various alkyl glycoside products.

Even when glycoside products are originally prepared (or are subsequently decolorized in accordance with one or more of the procedures set forth above) in a fashion which results in initial color characteristics acceptable for certain applications, such products nonetheless commonly exhibit a propensity to discolor (i.e., darken) as a function of time even under relatively mild storage conditions (e.g., at neutral or slightly acidic pH and ambient conditions, i.e., 20° C.-35° C.). The propensity to discolor is greatly accentuated (i.e., in terms of the intensity and rapidity thereof) by exposure to elevated temperatures (such as, for example, in the range of 35° C. to 100° C. or more) and/or exposure to relatively strong alkaline aqueous environments (i.e., pH of 8 to 12). Generally speaking, the extent of discoloration is related to the severity of the pH/temperature/time to which the glycoside product is exposed. In U.S. Pat. No. 4,557,729 to McDaniel et al. (issued Dec. 10, 1985), the aforementioned problem of color deterioration of glycoside products during storage thereof is discussed and a method for obviating such problem is disclosed which entails first bleaching the glycoside product of interest with an oxidizing agent such as ozone, hydrogen peroxide, hypochlorite, etc., and thereafter exposing the resulting bleached glycoside product to a source of sulfur dioxide (e.g., sulfur dioxide gas, sodium sulfite, sodium metabisulfite, sodium hydrosulfite, etc.) to stabilize said glycoside product against color degradation. Another McDaniel et al. patent, U.S. Pat. No. 4,904,774, notes the discoloration tendency of glycosides which have been decolorized by bleaching with peroxide materials such as hydrogen peroxide, upon exposure to high temperatures, and proposes color reduction by hydrogenation under catalytic hydrogenation conditions using materials such as Raney nickel or sodium borohydride. U.S. Pat. No. 4,990,605 to Lueders (issued Feb. 5, 1991) describes a method of manufacturing light colored alkyloligoglycosides by treatment with activated carbon followed by distillation and bleaching with a peroxide compound, preferably hydrogen peroxide, at temperatures of 50° to 100° C. under neutral or alkaline pH. Example 1, and comparative Example A, illustrates and compares the process with and without the activated carbon treatment.

The overall process to prepare light colored alkylpolyglycoside surfactants accordingly typically involves reaction of an alcohol with a saccharide in the presence of an acid catalyst followed by neutralization of the acid catalyst, removal of the alcohol and bleaching of the resultant substantially alcohol-free alkylpolyglycoside product, followed usually by a stabilization treatment to provide color stability. In the past, the process has been conducted as a batch process, and while it was recognized that a continuous process would be desirable, no practical continuous process has been developed to provide a very light colored alkylpolyglycoside surfactant product.

BRIEF SUMMARY OF THE INVENTION

Figure 1:
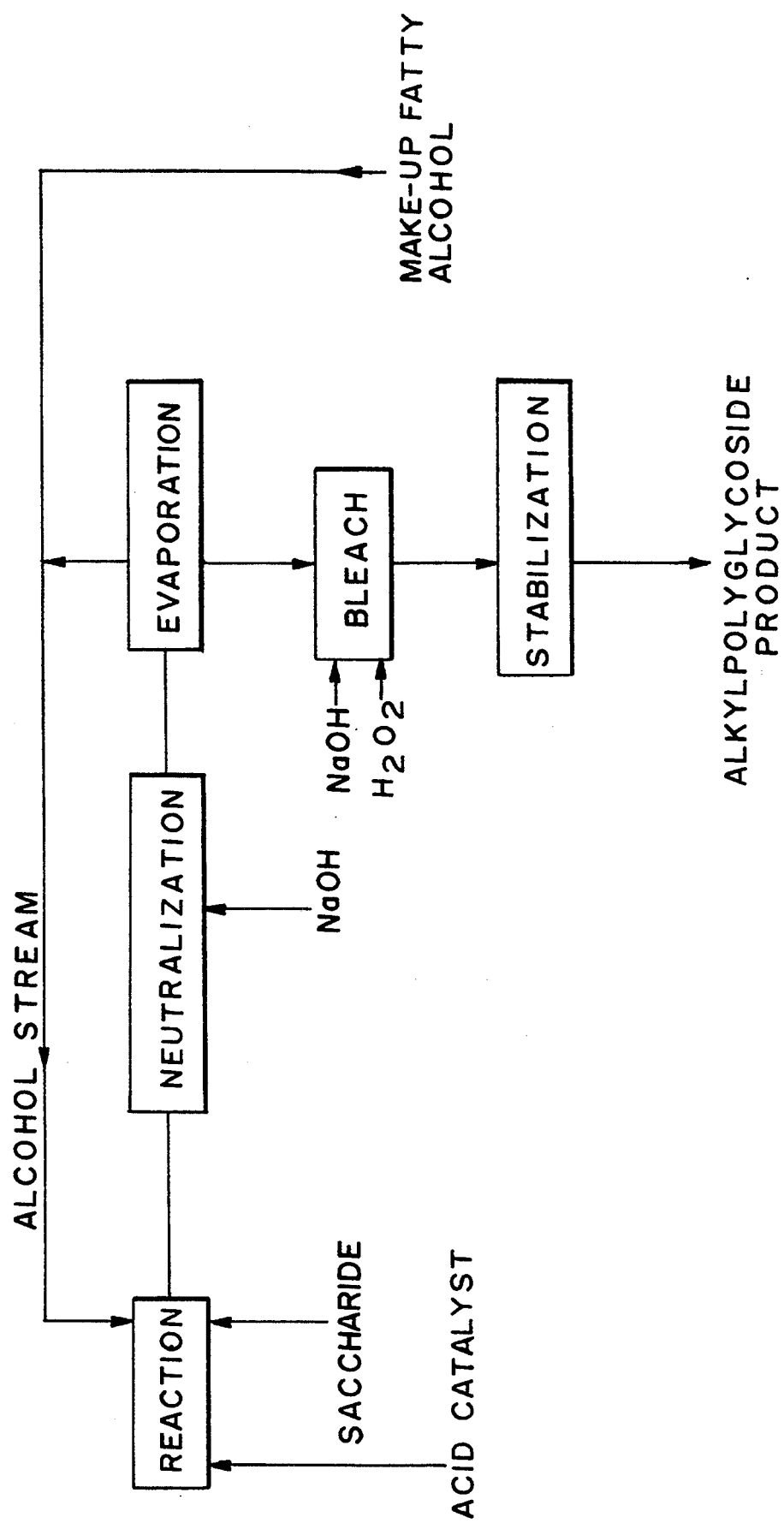
FIG. 1 is a diagrammatic flow chart of the overall process of preparation of a light color, stable, alkylpolyglycoside product showing the reaction of the alcohol and saccharide in the presence of an acid catalyst, followed by neutralization, removal of alcohol by evaporation, the bleaching process of the present invention and subsequent stabilization.

It has now been discovered that alkylpolyglycosides can be continuously bleached in a well-mixed, pressurized, vessel by metering in a crude alkylpolyglycoside feed (preferably substantially alcohol-free), preferably hydrogen peroxide (as the peroxy bleaching agent), and caustic and in the presence of more than about 250 ppm Mg (in the MgO form) per pound dry solids crude, into a bleaching matrix. The caustic addition is adjusted to maintain the reaction pH above 9, preferably above 10, by metering in from about 1.0 to about 1.2 moles of caustic per mole of peroxide and about 0.25 to about 2% wt./wt. peroxide per pound of dry solids polyglycoside. The pressure of the reaction mixture builds due to liquid hydraulics, including the water vapor pressure and oxygen generated from degradation of hydrogen peroxide and is controlled at an elevated, economical level. Based on the vessel pressure control, the bleached product is vented off as a foamy liquid and subjected to further downstream processing, such as stabilization.

The continuous process of this invention avoids the disadvantages of previous approaches involving batch processing. The present process allows for bleaching at temperatures which minimize discoloration and handling problems below about 120° C., preferably below 100° C. and most preferably in the range of about 90° to about 100° C., the nominal temperature limit of atmospheric pressure bleaching due to foam expansion and boiling. While the choice of operating temperature is primarily an economical consideration, it must balance investment capital (smaller reactor, smaller agitator, higher pressure reactor system and more reactor heating/cooling equipment with higher temperature) versus operating costs (higher hydrogen peroxide consumption, more product degradation, higher heating and cooling duties and less agitation power with higher temperature). In a production mode, where the product rate and equipment volume is fixed, the final product color is controlled by adjustment of the combination of the reactor temperature, reactor pressure and hydrogen peroxide dosage, which will be discussed in more detail hereinafter.

The use of a continuous tank reactor with the bleaching matrix, which includes the crude feed, peroxide, caustic and the Mg, provide a significant improvement in bleaching efficiency, improving the overall bleaching efficiency beyond that possible in a batch reaction. Another advantage of this continuous process is that it provides a repeatable and less operationally intensive processing technique. Also, the use of a pressure vessel provides the ability for bleaching to be conducted at temperatures greater than 100° C., thereby decreasing processing time by accelerating bleach reaction kinetics. Furthermore, the use of a pressure vessel lowers the volume of foam generated during this bleaching process, thereby reducing the required size of the vessel and the apparent viscosity of the foam. Reduction of the foam viscosity improves vessel agitation efficiency and heat transfer of the foamy liquid.

DETAILED DESCRIPTION AND PREFERRED EMBODIMENTS

Other than in the operating examples, or where otherwise indicated, all numbers expressing quantities, or reaction conditions used herein are to be understood as modified in all instances by the term "about."

In view of the Summary above, it is accordingly an object of the invention to provide an improved process for preparing light colored alkylpolyglycosides of a saccharide reacted with an alcohol in the presence of an acid catalyst at elevated temperatures, after which the acid catalyst is neutralized and the excess alcohol removed, and the substantially alcohol-free alkylpolyglycoside product is bleached and stabilized, in which the improvement comprises a controlled, continuous, bleaching step wherein said alkylpolyglycoside is bleached at an alkaline pH and elevated temperature with a peroxy bleaching agent preferably in the presence of magnesium in the form of the oxide, MgO.

As described in the related art section above, the initial reaction product of the alcohol and saccharide in the presence of an acid catalyst results in a glycoside product. The product is a mixture of a monoglycoside of the alcohol and various higher degrees of polymerization (DP) polyglycosides in progressively decreasing mole percentage amounts, i.e., the diglycoside (DP2), the triglycoside (DP3) and the higher polyglycosides (DP4 and higher). The typical, statistical distribution of the various oligomers provided referred to as a Flory distribution. While the specific distribution of the various fractions may vary somewhat for various reaction products, the overall distribution curve is the same, though the average DP of the reaction mixture may vary due to the differing distribution of the various fractions, i.e., DP1, DP2, DP3 and higher fractions. Typically, the Flory distribution of the reaction product after removal of the excess alcohol will have an average degree of polymerization above 1.2, i.e., about 1.4, with a monoglycoside content in the range of about 50–70% by weight of the glycoside product. Commercially available products typically have an average Flory DP of about 1.3–1.7.

The glycoside products of the reaction of an alcohol and saccharide may be represented by the formula I:

$$ROG_x \qquad (I)$$

wherein R is a residue of an alcohol, O is oxygen, G is a glycoside residue, and x is the average degree of polymerization (DP) resulting from weighting of the various mono-, di-, tri- and higher glycoside fractions present in the product and is a number of from about one to about three.

The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycoside having correspondingly more rings, the average of which in the currently available commercial product therefore being typically greater than about 1, generally in the order of about 1.2 to about 1.7, with preferred mixtures at about 1.3 to about 1.7.

The alkyl polyglycoside products represented by the formula above contain a lipophilic group, the R group, and a hydrophilic group, the $OG_x$ group. For detergent or surfactant-use application, the product should have a hydrophilic-lipophilic balance (HLB) of from about 10 to about 16, and preferably about 11 to about 14. The HLB value of a product may be calculated by the formula $$HLB = \frac{([MW_{AGU}] \times DP + MW_o)}{(([MW_{AGU}] \times DP + MW_o) + MW_R)} \times 100/5$$

where AGU is typically the anhydro glucose unit in G having a molecular weight of 162, $MW_o$ is the molecular weight of oxygen and $MW_R$ is the molecular weight of the R group, and DP is the average degree of polymerization as predicted by Flory's statistical treatment.

The lipophilic R groups in the alkyl polyglycosides are derived from alcohols, preferably monohydric, for the detergent, surfactant-use applications and should contain from about 8 to about 20, preferably about 9 to about 18 carbon atoms, with an average of about 10 to about 13 being most preferred, to provide R groups of sufficient length for detergent, surfactant-use applications. While the preferred R groups are saturated aliphatic or alkyl, there may be present some unsaturated aliphatic hydrocarbon groups. Thus, the preferred groups are derived from the fatty alcohols derived from the naturally-occurring fats and oils, such as octyl, decyl, dodecyl, tetradecyl, hexadecyl, octadecyl, oleyl and linoleyl, but R groups may be derived from synthetically produced Ziegler alcohols or oxo alcohols containing 9, 10, 11, 12, 13, 14 or 15 carbon atoms. The alcohols of naturally-occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process contain both an odd and even number of carbon atoms such as the $C_9$, $C_{10}$, $C_{11}$ mixtures, which are also available commercially.

Glycoside products suitable for treatment in accordance with the present invention also include derivatives of products of the formula I above including, for example, those in which one or more of the normally free (i.e., unreacted) hydroxyl groups of the saccharide moiety, G, have been alkoxylated, preferably, ethoxylated or propoxylated, so as to attach one or more pendant alkoxy or polyalkoxy groups in place thereof. The formula (I) above, in order to encompass both alkoxylated and non-ethoxylated products, may be modified to the formula II:

  (II)

where R, O, G and x are as defined earlier, $R^1$ is a divalent hydrocarbon radical of the alkoxylating agent, typically containing from 2 to about 4 carbon atoms and y is a number having an average value of from 0 to about 12, more preferably 0 to about 5. When y is 0, the formula reduces to formula I above and the product is non-alkoxylated.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g. methyl glycoside, ethyl glycoside, propyl glycoside, butyl glycoside, etc.), oligosaccharides (e.g. sucrose, maltose, maltotriose, lactose, zylobiose, melibiose, cellobiose, raffinose, stachyose, etc.) and other polysaccharides. Such saccharide reactants may be employed in dry (e.g. anhydrous) form or, if desired, may be employed in the form of hydrated solids or aqueous solutions thereof. If utilized in the form of a solution, it is preferred that the resulting reaction mixture contain only small amounts of water, i.e., less than about 1% by weight, preferably less than about 0.5% i.e. less than 0.25 or 0.1%.

While the preparation of the initial alkyl glycosides reaction mixture employed in the present invention forms no direct part of the present invention, a brief description generally of the preparation follows. The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. Preferably, the ratio of alcohol to monosaccharide will be chosen to allow the production of an alkyl glycoside product having a DP between about 1.2 to about 1.7, and more preferably about 1.3 and about 1.6.

The reaction, as shown in FIG. 1, between the hydrophobic alcohol reactant and the saccharide reactant to form the glycoside surfactant is typically conducted at an elevated temperature and in the presence of an acid catalyst. As a general rule, said reaction is preferably conducted at a temperature of from about 80° to about 140° C., preferably about 90° to about 120° C., and at pressures (about 10 to about 100 mm Hg absolute), which facilitate water removal, while at the same time maintaining the desired reaction temperatures.

Acid catalysts suitable for use include strong mineral acids such as hydrochloric acid, sulfuric acid, nitric acid, phosphoric acid, hypophosphorous acid, etc.; strong organic acids such as para toluenesulfonic acid, methanesulfonic acid, triflouromethanesulfonic acid, mono- or polyalkylated aryl mono- or polysulfonic acids such as dodecylbenzenesulfonic acid, etc.; and macroreticular acidic ion exchange resins such as macroreticular sulfonic acid ion exchange resins, perfluorinatedsulfonic acid resins, etc. Typically, said acid catalyst will be employed in an amount ranging from about 0.0005 to about 0.03 (preferably from about 0.002 to about 0.015) moles thereof per mole of saccharide used.

Typically, the above-described reaction process will be conducted over a reaction period of from about 1 to about 20 (preferably from about 2 to about 10) hours. Upon completion of the reaction, the acid catalyst is typically neutralized as indicated in FIG. 1 by an alkaline substance, preferably an alkali metal hydroxide such as sodium hydroxide, used in an amount about equal, on a stoichiometric basis, to the amount of material needed to neutralize the catalyst. For the present invention, most preferably the mixture is neutralized and adjusted to a pH in the range of about 9 to about 10 with an alkali metal hydroxide and alkaline earth metal oxide, such as magnesium oxide, prior to removal of the alcohol.

After neutralization of the acid catalyst, typically excess unreacted alcohol is removed. Alcohol removal is generally accomplished by evaporation, e.g. distillation, of the alcohol as indicated in FIG. 1. The use of a wiped film or thin film evaporator is particularly convenient for this purpose, preferably operated at about 150°-220° C. and about 0.1 to about 50 mm Hg pressure. More generally pressures of about 1 to about 100 mm Hg and temperatures of about 140° to about 230° C. may be employed. Other methods of removal of the alcohol may be employed including distillation techniques and supercritical extraction under conditions for removing alcohol to levels below about 5%, more desirably below about 2% by weight to about 0.5%.

At this point, the resulting commercial product, substantially devoid of alcohol, is typically a mixture of alkyl glycosides, in which for purposes of this invention the average alkyl group will contain from about 8 to about 20, preferably about 9 to about 18, most preferably an average of about 10 to about 13, carbon atoms, having the typical Flory distribution discussed earlier above.

After removal of the excess alcohol to a level less than about 5% and preferably less than about 1% by weight, the substantially alcohol-free product is then bleached to a light color by the continuous bleaching process of the present invention. The present invention is also applicable to glycoside products which have been molecularly distilled to further remove a portion of the monoglycoside present, particularly those in which sufficient monoglycoside is removed to provide a mixture of alkylpolyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions can be prepared by separation of the monoglycoside from the original reaction mixture of alkyl monoglycoside and alkyl polyglycosides after removal of the alcohol. This separation may be carried out by molecular distillation which normally results in the removal of about 70-95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in commonly assigned copending application Ser. No. 07/810,588, filed on Dec. 19, 1991, now U.S. Pat. No. 5,266,690, the entire contents of which are incorporated herein by reference. Molecular distillation as described therein is a short path, high vacuum distillation. On a laboratory scale, pressures of about 0.1 mbar and lower may be employed. On a commercial scale, pressures will desirably be in the range of 0.01 mbar and lower, preferably about 0.001 mbar or lower. In the molecular distillation, a very short distance is employed between the vaporization and condensing surfaces, which is as close as possible. In practice the actual gap is bounded by about 0.1 to about 10 times the mean free path of distilling molecules which is defined by kinetic theory. The residence time is as short as possible to minimize thermal degradation of the alkyl polyglycosides, less than about 2 minutes and preferably less than about 15 seconds. With removal of at least about 50% of the monoglucosides, the molecularly distilled products will have an average DP of at least about 1.8 and about at least 0.2 units higher than the average DP of the initial feed to the molecular still. If the amount of monoglycoside separated from the original reaction mixtures is in a sufficient amount to provide that the monoglycoside retained in the resulting product is less than the total of DP2 and DP3 fractions, or more preferably, less than that of the DP2 fraction, it can be readily seen that a "peaked" distribution results i.e. that the DP2 and DP3 distribution now illustrates a reduced or non-monoglycoside "peaked" distribution in the resulting products, which retain the DP4 and higher fractions in the resulting products prepared by molecular distillation.

The present continuous bleaching process is accordingly applicable to alkylpolyglycosides from which only the excess alcohol has been removed or those which have been treated so as to remove at least a portion, including removal of a significant portion of monoglycoside.

In still another embodiment, the continuous process of bleaching is also applicable to compositions comprised of a mixture of two or more of at least binary components of alkylpolyglycosides wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated. Such compositions are disclosed in commonly assigned application Ser. No. 07/774,430, filed on Oct. 10, 1991, now abandoned, the entire contents of which are incorporated herein by reference. As described therein, in commercial practice alkylpolyglycosides are prepared from binary or ternary mixtures of alcohols providing the corresponding mixtures (binary or ternary) of alkylpolyglycosides. The application accordingly describes the preparation of alkylpolyglycoside compositions having a preselected or predetermined average alkyl chain length and surfactant properties prepared from commercially available at least binary mixtures. After selecting the predetermined average carbon chain length of the alkyl moiety, the composition having the desired detergent or surfactant properties is prepared by mixing two or more of at least binary components, each binary component having an average alkyl chain length such that when mixed the amounts of the binary components are effective to provide the predetermined selected average alkyl moiety and surfactant properties. Thus, the composition may contain a mixture of $C_8$–$C_{10}$, $C_{10}$–$C_{12}$, $C_{12}$–$C_{13}$, $C_{12}$–$C_{16}$, $C_{12}$–$C_{14}$, $C_{14}$–$C_{15}$, $C_{16}$–$C_{18}$, as well as one containing $C_9$–$C_{10}$–$C_{11}$ and $C_{12}$–$C_{14}$–$C_{16}$ alkylpolyglycosides and the like.

Thus, the bleaching process of the present invention, while preferably useful as a step in the overall preparation of alkylpolyglycosides including the initial reaction, neutralization, alcohol removal, decolorization and stabilization (as shown in FIG. 1), is also applicable to alkylpolyglycosides of (a) a single alkyl group, (b) commercially available mixtures of alkylpolyglycosides having two or more different alkyl groups and (c) to molecularly distilled products in which the products have a peak of the DP2, or DP2 and DP3 components therein.

In its broadest embodiment, the present invention is a method of reducing the color of an alkylpolyglycoside comprising the steps of
(a) providing an aqueous solution of the alkylpolyglycoside;
(b) continuously introducing said aqueous solution from step (a) to a bleaching zone maintained at an elevated temperature suitable for bleaching;
(c) adjusting and maintaining the pH of the aqueous solution in said bleaching zone at an alkaline pH;
(d) contacting the aqueous solution at the alkaline pH with a peroxy bleaching agent in an amount effective to bleach and reduce the color of the alkylpolyglycoside; and
(e) continuously removing alkylpolyglycoside from said bleaching zone wherein the alkylpolyglycoside has a Klett color below about 50 and a residual bleaching agent level below about 1000 ppm, preferably below about 500 ppm.

In the process above, the alkylpolyglycoside is one obtained from the reaction at elevated temperatures of an alcohol and saccharide in the presence of an acid catalyst as discussed earlier above, after neutralization of the acid catalyst and removal of substantially all excess alcohol. In vessel 1 of FIG. 2, the alkylpolyglycoside is diluted with water to form an aqueous solution containing about 30 to about 85% by weight dry solids (ds) alkyl polyglycoside, preferably about 50 to about 75% and most preferably about 53 or 55 to about 73%. The alkylpolyglycoside product from the evaporation of the alcohol contains less than about 5% alcohol, preferably less than about 2% and most preferably less than about 1% to about 0.5%, thereby containing from about 95 to about 99.5% alkylpolyglycoside. The alkylpolyglycoside product now substantially alcohol-free, is removed from the evaporation zone at a temperature of about 390° F., plus or minus about 30° F., about the temperature employed in the evaporation step. The water employed to provide the aqueous solution of alkylpolyglycoside for the bleaching process of the present invention, may be pre-heated to a temperature of about 70° to about 150° F. in a preheater 2 in FIG. 1.

After the process of reaction of the alcohol and saccharide to form the alkylpolyglycoside, the acid is neutralized as discussed earlier above, preferably with an alkali metal hydroxide, such as sodium hydroxide. Most preferably the neutralization is carried out with a mixture of sodium hydroxide and an alkaline earth metal oxide, such as magnesium oxide, to a pH level of about 9 to about 11 or 12. The magnesium oxide is employed in an amount effective to provide about 250 to about 1000 ppm, or less, of magnesium in the product after evaporation and removal of the alcohol. The aqueous solution of the substantially alcohol-free alkylpolyglycoside and the preheated water will accordingly, preferably contain less than 1000 ppm magnesium and more preferably about 500 to about 700 ppm for solution containing about 50% to about 70% d.s. alkylpolyglycosides.

The temperature of the aqueous solution is controlled and maintained at a temperature about the temperature at which the bleaching step will be conducted, and the aqueous solution is then introduced into a vessel or bleaching reactor 3 which is maintained at the bleaching temperature of about 85° to about 105° C., preferably about 88° to about 93° C. (about 190° to about 200° F.), most preferably at about 88° C. (190° F.).

Figure 2:
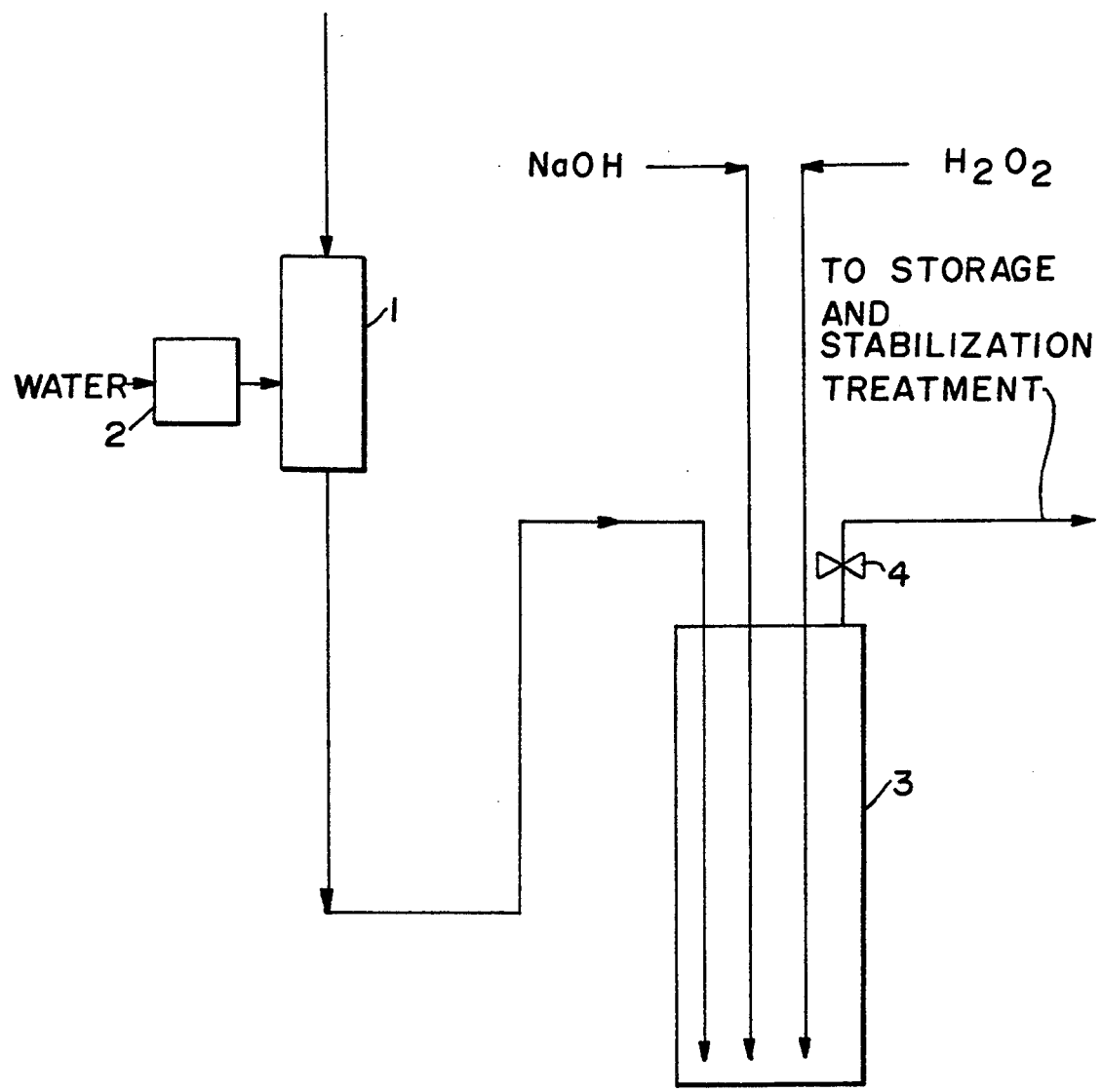
FIG. 2 of the drawing is a more detailed flow chart of the continuous bleaching step of the present invention to provide a light colored alkylpolyglycoside surfactant.

As shown in FIG. 2, the aqueous solution is introduced into the bleaching reactor 3. In start-up of the continuous process, the reactor will be filled to a level above the agitator (not shown) in vessel 3 before the caustic and bleaching agent (preferably NaOH and $H_2O_2$) are introduced into the reactor vessel. The pH of the aqueous solution is adjusted to a level of about 10 to about 11.5, preferably about 10.2 to about 10.8, most preferably about 10.3 to about 10.7, (i.e. about 10.5) and maintained at this level during the bleaching process by the use of alkali metal hydroxide, preferably NaOH as shown in FIG. 2. The preferred bleaching agent is hydrogen peroxide, $H_2O_2$, shown in FIG. 2. The amounts of NaOH and $H_2O_2$ are controlled and metered into the vessel 3 in amounts effective to maintain the pH level at the desired level and to effect the reduction in color to the desired level. The hydrogen peroxide preferably in a 35% aqueous solution, will be employed in a weight per weight (wt/wt) dry solids alkylpolyglycoside of about 0.25 to about 2% wt/wt, more desirably about 0.6 to about 1.25% and most preferably at about 1%. The sodium hydroxide will be employed in an amount of about 0.9 to about 1.2 moles NaOH per mol $H_2O_2$, preferably at about 1.1 moles NaOH per mole $H_2O_2$.

If magnesium is already present at the appropriate level as a result of the use in the neutralization of the acid catalyst after the reaction wherein the alkylpolyglycoside is prepared from the alcohol and saccharide reaction, no further control thereof is required. Adjustment of the magnesium level, if necessary, can preferably be made by adding a source of magnesium, such as MgO or $MgSO_4$ to the aqueous solution prior to introduction to the reactor vessel 3, during preparation of the aqueous solution. However, if convenient to do so, the magnesium oxide can be introduced directly into the bleaching zone reactor vessel 3. The lower levels of MgO result in more decomposition of peroxide during the reaction and accordingly to achieve the same color conversion will require a higher peroxide dosage and/or higher pH resulting in increased cost of the operation. Operation above 250 ppm and less than 1000 ppm results in an optimum balance.

The hydrogen peroxide and sodium hydroxide are typically injected simultaneously and the process proceeds with evolution of oxygen from the hydrogen peroxide addition, which causes the reaction pressure to rise. Foaming occurs in the reactor, but foaming is minimized by not automatically venting the reactor to maintain atmospheric pressure. As shown in FIG. 2, a valve 4 which contains a pressure relief valve permits the pressure in the reactor to rise and be maintained at about 40 psig, more preferably about 20 psig. This minimizes foam and permits efficient bleaching.

The efficiency of the hydrogen peroxide bleaching is influenced by the concentration of residual peroxide, pH and reaction temperature. At the pH level and temperatures discussed above, residual peroxide levels are maintained above 200 ppm to about 1500 ppm, preferably below 1000 ppm and most preferably at about 200 to about 400 for greatest efficiency.

In the continuous process, residence time is largely fixed by the product rate from the evaporator where the alcohol is removed. Residence times on the order of about 5 to about 15 hours are generally used with about 5 to about 7.0 being preferred at temperatures of about 200° to about 210° F., most preferably about 6.0 to about 6.5 at the temperatures of about 205° F. and about 10 to about 12 at temperatures of about 190° to about 200° F., with about 12 at about 190° F., pH and peroxide levels preferred as discussed above and with feed rates of substantially alcohol-free alkylpolyglycoside melt from the evaporation above. The temperature is controlled and maintained at the preferred level and the feed of caustic and peroxide controlled and maintained to provide the preferred pH and peroxide levels, at target steady state values of about 10.7 to about 11.0 pH and about 200 to about 400 ppm respectively. These conditions will provide product of the desired reduced color, which can be monitored throughout the process by sampling and determining the color. The aqueous solution fed to the bleaching vessel will be dark having an extinction coefficient at 470 nm in the range of about 10 to about 15, typically at about 12.5 to about 13. The target steady state value for extinction coefficient of the product at pH of 7 is from about 0.025 to about 0.15, and provides a Klett color of 50 or less preferably in the range of about 5 to about 30.

After completion to the desired bleaching level, the product exiting the continuous stirred bleach reactor 3 is cooled to about 150° F. (about 65° C.) in preparation for completion of the finishing process which includes a stabilization treatment, to stabilize the color against any reversion to a darker color. Such treatment typically involves catalytic hydrogenation or treatment with a stabilizing compound, such as alkali metal borohydrides to further reduce color and stabilize the color against deterioration over long periods of storage. After the finishing process, the pH and concentration of the alkylpolyglycoside surfactant is adjusted and placed in storage for sale. In a borohydride stabilization, a peroxide bleached alkylpolyglycoside solution of about 50 to about 55% actives concentration, and a pH of about 10 and residual peroxide concentration below about 50 ppm, and preferably below about 25 ppm is adjusted to a pH of about 7 with sulfuric acid to eliminate any haze, after which the product is adjusted to a pH of about 10 and treated with a sodium borohydride solution until the borohydride concentration is substantially zero.

The invention can best be illustrated by means of the following examples in which all parts and percentages are by weight unless otherwise specified. In the preceding description, references have been made to color determination expressed as extinction coefficient and as Klett color. These color determinations are conducted as set forth in Examples A and B below:

EXAMPLE A

Extinction Coefficient Color Determination

The extinction coefficient method is a measure of color by absorption. This method uses absorbance at 470 nm, the fraction of dry solids, and 'as is' sample weight, diluted sample weight, and densities to arrive at the extinction coefficient.

The determination is made employing a Spectronic 20, Bausch & Lomb, Spectrophotometer (Catalog No. 33-31-72 or equivalent) and Dispo Culture Tubes for measurement, 13×100 mm. (VWR Products, Catalog No. 60825-571 or equivalent). The dry solids weight fraction of the as is sample is determined. A sample is diluted with a 3/1(v/v) isopropanol/water blend to obtain a clear solution which will give a transmittance between 15% and 85% on the Spectronic 20. The weight of the 'as is' sample and of the diluted sample is noted and the density (g/ml) of the final dilution sample is determined. The absorbance of the clear diluted sample at 470 nm is measured in the Spectronic 20. The extinction coefficient (ec) is calculated using the following formula:

$$ec = \frac{(\text{absorbance}) * (\text{grams final diluted solution})}{(\text{fraction } DS \text{ of as is sample}) * (\text{grams as is sample}) * (\text{density of final, diluted solution})}$$

EXAMPLE B

Klett Color Determination

In this method the procedure is an empirical measurement of color (broad band absorbance) using a Klett-Summerson Photoelectric Colorimeter, Glass Cell Model 900-3, using a 400–450 nm blue filter No. RS-42 and a Klett cuvette test cell (rectangular, 8×4×2 cm glass cuvetti, Klett part No. 901, optical path length, 4 cm). After calibration and preparation of the sample cuvette, the absorbance is measured at 5% actives and pH of 7 and the scale reading reported as "Klett color (4 cm )."

EXAMPLE 1

This example is an illustration of a continuous steady-state process of bleaching of a substantially alcohol-free alkylpolyglycoside melt subsequent to removal of the alcohol by an evaporation process. Softened Water (2900#/hr) was injected into a stream of $C_{12}$–$C_{16}$ alkylpolyglucoside melt (3250#/hr). The resulting 6150#/hr blend containing 0.23% residual fatty alcohol, was dark in color (extinction coefficient @ 470 nm=12.7), and was passed through an in-line static mixture and through a dip tube into the bottom of a jacketed pressure vessel, equipped with temperature control, an agitator and dip-tube chemical addition lines (50% caustic and 35% peroxide). After about four hours, sufficient material was present to start the agitator, and the temperature controller was set at 190° F. and the overflow top exit valve set to open at 20 psi. Caustic was added at 200#/hr until the pH of the mixture, measured on an "as is" basis at room temperature, was above 10.8, at which time the 50% caustic flow was reduced to 77#/hr and the peroxide flow was started at 90#/hr. These flows were maintained throughout the run with minor adjustments to maintain target steady-state values of color, pH, residual peroxide of e.c. (@ pH=7)=0.05–0.15, pH=10.7–11.0, and residual $H_2O_2$=200–400 ppm respectively. These targets attained after about 1.25–1.5 reactor volumes, and the material exiting the continuous stirred bleach reactor was cooled to about 150° F. in preparation for completion of the finishing process.

As can be seen from the foregoing description of the related art and the present invention, including the examples of the continuous process, a highly efficient bleaching process is developed which results in an unexpected reduction in color from a dark brown (extinction coefficient of about 10 to about 15 at 470 nm on a 50-55% active aqueous solution) to a very light or white, slightly hazy, solution of an extinction coefficient color on the order of about 0.025 to about 0.15. The color as determined by the Klett method is below about 50 and in the range of about 5 to about 30.

We claim:

1. A method of reducing the color of an alkylpolyglycoside comprising the steps of
    (a) providing an aqueous solution of the alkylpolyglycoside;
    (b) continuously introducing the aqueous solution from step (a) to a bleaching zone maintained at a temperature of about 85° to about 105° C.;
    (c) adjusting and continuously maintaining the pH of the aqueous solution in said bleaching zone at a pH of about 10 to about 11.5;
    (d) contacting the aqueous solution with a peroxy bleaching agent in an amount effective to bleach and reduce the color of the alkylpolyglycoside and in the presence of more than about 250 ppm and less than about 1000 ppm Magnesium (Mg); and
    (e) continuously removing alkylpolyglycoside from said bleaching zone, wherein the alkylpolyglycoside has a Klett color below about 50, an extinction coefficient color from about 0.025 to about 0.15 and a residual bleaching agent level below about 1000 ppm.

2. A method as defined in claim 1, wherein the alkylpolyglycoside in step (a) is the reaction product of an alcohol and a saccharide in the presence of an acid catalyst having an extinction coefficient color of about 10 to about 15.

3. A method as defined in claim 2, wherein said alkylpolyglycoside in step (a) contains less than about 5% by weight of the alcohol from the reaction of the alcohol and saccharide.

4. A method as defined in claim 3, wherein the alkylpolyglycoside in step (a) contains less than about 1% by weight of the alcohol.

5. A method as defined in claim 3, wherein said aqueous solution in step (a) contains about 30% to about 85% by weight alkylglycoside.

6. A method as defined in claim 5 wherein said aqueous solution contains about 50 to about 75% alkylglycoside.

7. A method as defined in claim 6 wherein said aqueous solution contains about 55% by weight alkylglycoside.

8. A method as defined in claim 1 wherein the temperatures in said bleaching zone is maintained at a temperature of about 88° to about 93° C.

9. A method as defined in claim 8 wherein the temperature is maintained at about 88° C.

10. A method as defined in claim 1, wherein the pH of the aqueous solution in the bleaching zone is maintained at about 10.2 to about 10.8.

11. A method as defined in claim 10 wherein the pH is maintained at about 10.5.

12. A method as defined in claim 10 wherein the aqueous solution in the bleaching zone contains Mg in the form of MgO in an amount of about 250 to about 1000 ppm.

13. A method as defined in claim 1 wherein the bleaching agent is hydrogen peroxide.

14. A method as defined in claim 13, wherein the pH is maintained in the bleaching zone with sodium hydroxide.

15. A method as defined in claim 14, wherein the hydrogen peroxide is employed in an amount on a weight per weight basis of peroxide to dry solids alkylglycoside of about 0.25 to about 2% and the sodium hydroxide is employed in an amount of about 0.9 to about 1.2 moles of sodium hydroxide per mole of hydrogen peroxide.

16. A method as defined in claim 15 wherein the hydrogen peroxide is employed at about 1% and the sodium hydroxide is employed at about 1.1 moles sodium hydroxide per mole of hydrogen peroxide.

17. A method as defined in claim 15 wherein the aqueous solution in the bleaching zone contains Mg in the form of MgO in an amount of about 250 to about 1000 ppm.

18. A method as defined in claim 1 wherein a pressure is maintained in the bleaching zone up to about 40 psig and the residence time of the alkylglycoside in the bleaching zone is about 5 to about 15 hours.

19. A method as defined in claim 18 wherein the pressure is maintained in the bleaching zone at about 20 psig and the residence time is about 6 to about 6.5 hours.

20. A method as defined in claim 1 wherein
    (1) the alkylglycoside in step (a) has an extinction coefficient color of about 10 to about 15, contains less than about 5% of the alcohol from which the alkylglycoside was prepared, and is contained in the aqueous solution of step (a) in an amount of about 30 to about 85% by weight;
    (2) the temperature in the bleaching zone is maintained at about 88° to about 93° C.;
    (3) the pH of the aqueous solution in the bleaching zone is maintained at about 10.2 to about 10.8 with sodium hydroxide;
    (4) the bleaching agent is hydrogen peroxide employed in an amount on a weight per weight basis of peroxide to dry solids alkylglycoside of about 0.25 to about 2% and the sodium hydroxide in (3) is employed in an amount of about 0.9 to about 1.2 moles sodium hydroxide per mole of hydrogen peroxide;
    (5) the aqueous solution in the bleaching zone contains Mg in the form of MgO in an amount of about 250 to about 1000 ppm.
    (6) pressure is maintained in the bleaching zone up to about 40 psig and the residence time in the bleaching zone is about 10 to about 15 hours;
    (7) the alkylglucoside removed in step (e) has an extinction coefficient color from about 0.25 to about 0.15.

21. A method as defined in claim 20, wherein the alcohol in (1) is less than about 1% by weight and the aqueous solution in (1) contains about 55% by weight alkylglycoside; the temperature is maintained at about 88° C.; the pressure is maintained at about 20 psig; the residence time is about 12 hours; the hydrogen peroxide is employed in an amount of about 1% weight per weight basis of peroxide to alkylglycoside and the sodium hydroxide is employed in an amount of about 1.1 moles per mole of hydrogen peroxide; and the pH is maintained at about 10.5.

22. An alkylglycoside having a color reduced from an extinction coefficient color of about 10 to about 15 to an extinction coefficient color of about 0.025 to about 0.15.

* * * * *